United States Patent
Abe et al.

[11] Patent Number: 6,136,808
[45] Date of Patent: Oct. 24, 2000

[54] TAXANE DERIVATIVES

[75] Inventors: Atsuhiro Abe; Hideaki Shimizu; Seigo Sawada; Takanori Ogawa; Hiroshi Nagata, all of Tokyo, Japan

[73] Assignee: Kabushiki Kaisha Yakult Honsha, Tokyo, Japan

[21] Appl. No.: 09/508,092

[22] PCT Filed: Sep. 17, 1998

[86] PCT No.: PCT/JP98/04180

§ 371 Date: Mar. 16, 2000

§ 102(e) Date: Mar. 16, 2000

[87] PCT Pub. No.: WO99/14209

PCT Pub. Date: Mar. 25, 1999

[30] Foreign Application Priority Data

Sep. 17, 1997 [JP] Japan ................................. 9-251804

[51] Int. Cl.$^7$ ...................... A61K 31/495; A61K 31/445; C07D 405/00; C07D 401/00; C07D 409/00

[52] U.S. Cl. .......................... 514/255; 514/320; 544/374; 544/365; 544/379; 546/196

[58] Field of Search ................... 514/255, 320; 544/374, 365, 379; 546/196

[56] References Cited

U.S. PATENT DOCUMENTS

| | | | |
|---|---|---|---|
| 4,942,184 | 7/1990 | Haugwitz et al. | |
| 5,243,045 | 9/1993 | Holton et al. | |
| 5,250,683 | 10/1993 | Holton et al. | |
| 5,968,931 | 10/1999 | Bouchard et al. | 54/226.8 |
| 6,017,935 | 1/2000 | Mastalerz et al. | 514/337 |
| 6,025,385 | 2/2000 | Shimizu et al. | 514/449 |

FOREIGN PATENT DOCUMENTS

| | | |
|---|---|---|
| 3-505725 | 12/1991 | Japan . |
| 5-239044 | 9/1993 | Japan . |
| 5-239055 | 9/1993 | Japan . |
| 6-199824 | 7/1994 | Japan . |
| 7-503477 | 4/1995 | Japan . |
| WO 93/16060 | 8/1993 | WIPO . |

OTHER PUBLICATIONS

J. Kant, et al., Tetrahedron Letters, vol. 35, No. 1, pp. 5543–5546, "A Chemoselective Approach to Functionalize C–10 Position of 10–Deacetylbaccatin III. Synthesis and Biological Properties of Novel C–10 Taxol® Analogues," 1994.

*Primary Examiner*—Deborah C. Lambkin
*Attorney, Agent, or Firm*—Oblon, Spivak, McClelland, Maier & Neustadt, P.C.

[57] ABSTRACT

This invention relates to a taxane derivative represented by the following formula (1):

(1)

(wherein A represents a substituted piperazino or piperidino group, X represents an alkyl, pyridyl, thienyl, furyl, cycloalkyloxy or the like and Y represents H or trialkylsilyl) and also to a drug containing the same.

This compound has high solubility in water and also has excellent antitumor activities.

11 Claims, No Drawings

TAXANE DERIVATIVES

This appln. is a 371 of PCT/JP98/04180 Sep. 17, 1998.

TECHNICAL FIELD

This invention relates to taxane derivatives having excellent solubility in water, and also to drugs containing the same.

BACKGROUND ART

Taxol (registered trademark) (i) represented by the following formula (i):

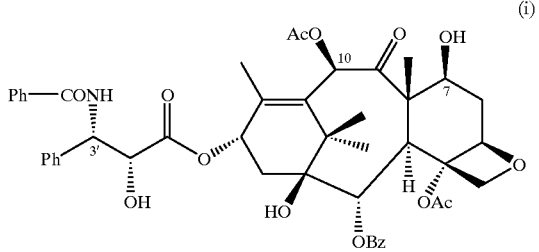

is a diterpenoid available by extraction from the bark of the Pacific yew tree, *Taxus brevifolia,* and was isolated and determined in structure for the first time in 1971 by Wall, et al. (J. Am. Chem. Soc., 93, 2325, 1971). It has been reported to exhibit high efficacy against ovarian cancer and breast cancer (Ann. int. Med. 111, 273, 1989).

Formulation of Taxol into an injection however requires a special solvent, as it is a compound sparingly soluble in water. Taxol is therefore accompanied by problems in that the production of an injection is difficult and side effects may be induced by a solvent.

A great deal of work has therefore been conducted in recent years with a view to developing a water-soluble derivative of Taxol (Nicolaou, et al., Nature, 364, 464, 1993). Under the current circumstances, however, no derivatives have been found yet to be equipped with satisfactory properties.

Accordingly, an object of the present invention is to provide a novel Taxol derivative having improved water solubility and high antitumor activities.

DISCLOSURE OF THE INVENTION

With the foregoing circumstances in view, the present inventors have proceeded with extensive research. As a result, it has been found that a derivative of taxane (general name of the Taxol skeleton) represented by the below-described formula (1) has water solubility and antitumor activities, each extremely higher than Taxol and is hence useful as a drug, leading to the completion of the present invention.

The present invention therefore provides a taxane derivative represented by the following formula (1):

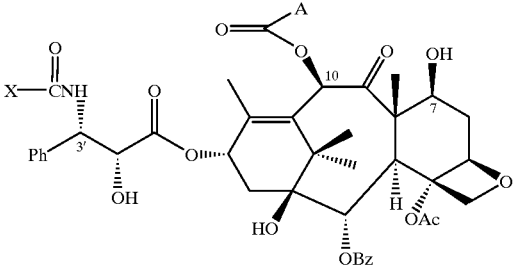

[wherein, A represents a group

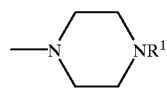

(in which $R^1$ represents a hydrogen atom, a substituted or unsubstituted alkyl group or a benzyloxycarbonyl group) or a group $$-N\underset{}{\bigcirc}-R^2$$

(in which $R^2$ represents an amino group, a mono- or di-alkylamino group or a cyclic amino group), X represents an alkyl group, a pyridyl group, a thienyl group, a furyl group, a cycloalkyloxy group, an isopropyloxy group, a neopentyloxy group or a tert-amyloxy group, Y represents a hydrogen atom or a trialkylsilyl group, Ac represents an acetyl group, Bz represents a benzoyl group, and Ph represents a phenyl group] or a salt thereof.

Further, the present invention also provides a drug comprising the taxane derivative represented by the formula (1) or the salt thereof as an active ingredient.

Still further, the present invention also provides an antitumor agent comprising the taxane derivative represented by the formula (1) or the salt thereof as an active ingredient.

Still further, the present invention also provides a drug composition comprising the taxane derivative represented by the formula (1) or the salt thereof and a pharmaceutically acceptable carrier.

Still further, the present invention also provides use of the taxane derivative represented by the formula (1) or the salt thereof as a drug.

Still further, the present invention also provides use of the taxane derivative represented by the formula (1) or the salt thereof as an antitumor agent.

Still further, the present invention also provides a method for the treatment of a tumor, which comprises administering, to a patient suffering from the tumor, an effective amount of the taxane derivative represented by the formula (1) or the salt thereof.

BEST MODES FOR CARRYING OUT THE INVENTION

The taxane derivative according to the present invention is represented by the formula (1). The alkyl group represented by $R^1$ as a substituent on the piperazino group among the groups represented by A may be an alkyl group having 1 to 10 carbon atoms, examples of which can include methyl, ethyl, n-propyl, i-propyl, n-butyl, i-butyl, sec-butyl, tert-butyl, n-pentyl, n-hexyl, n-heptyl, n-nonyl and n-decyl. Of these alkyl groups, those having 1 to 6 carbon atoms, especially those having 1 to 4 carbon atoms are preferred, with methyl and ethyl groups being more preferred. Illustrative of substituent or substituents of the alkyl group are monoalkylaminocarbonyl groups and dialkylaminocarbonyl groups. $C_{1-6}$ alkylaminocarbonyl groups can be mentioned as more preferred monoalkylaminocarbonyl groups, while di-($C_{1-6}$ alkyl)aminocarbonyl groups can be mentioned as more preferred dialkylaminocarbonyl groups.

As examples of the alkyl moiety of the mono- or di-alkylamino group represented by the substituent $R^2$ on the piperidino group among the groups represented by A, alkyl groups similar to those exemplified above as the alkyl group represented by $R^1$ can be mentioned, with methyl, ethyl, n-propyl and i-propyl being preferred. Examples of the cyclic amino group represented by $R^2$ include pyrrolidino, piperidino and morpholino groups.

Among the groups represented by A, particularly preferred examples include dialkylaminopiperidino, piperidinopiperidino, pyrrolidinopiperidino, morpholinopiperidino and N-alkylpiperazino groups.

As the alkyl group represented by X, groups similar to those exemplified above as the alkyl group represented by $R^1$ can be mentioned, with $C_{1-6}$ alkyl groups being more preferred. As the cycloalkyloxy group, $C_{4-6}$ cycloalkyloxy groups are preferred, with cyclopentyloxy and cyclohexyloxy groups being more preferred.

The group represented by Y is a hydrogen atom or a trialkylsilyl group, examples of which include tri($C_{1-6}$ alkyl) silyl groups. As Y, a hydrogen atom is particularly preferred.

Illustrative of the salt of the taxane derivative (1) according to the present invention are pharmaceutically acceptable salts, for example, anion salts such as hydrochloride, hydroiodide, tartrate, acetate, methanesulfonate, maleate, succinate and glutarate and salts with an amino acid such as arginine, lysine or alanine. Further, the taxane derivative or the salt thereof according to the present invention may exist in the form of a hydrate. The hydrate is also embraced in the present invention.

The taxane derivative (1) according to the present invention can be prepared, for example, in accordance with the following reaction scheme.

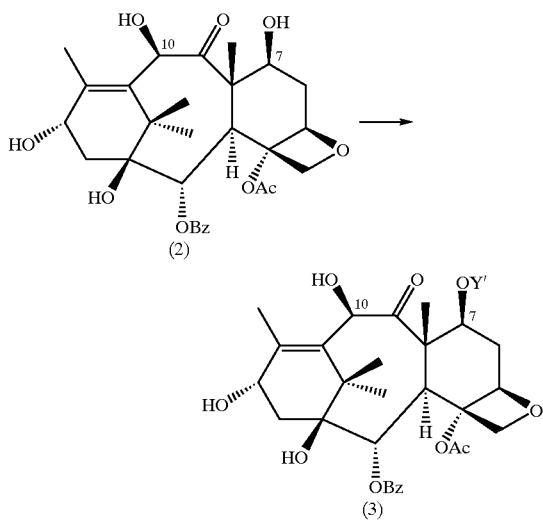

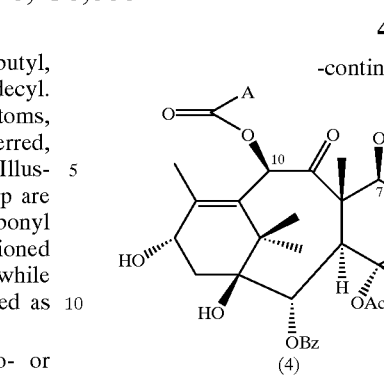

[wherein, A, Ac, Bz and Ph have the same meanings as described above; $R^3$ represents a hydrogen atom, an alkoxycarbonyl group or a benzyloxycarbonyl group; $R^4$ and $R^5$ each represents a hydrogen atom, an alkyl group, a halogenoalkyl group or an alkoxyphenyl group with the proviso that $R^4$ and $R^5$ do not represent a hydrogen atom at the same time or when either one of $R^4$ or $R^5$ represents a halogenoalkyl group or an alkoxyphenyl group, the other one is a hydrogen atom; and Y' represents a trialkylsilyl group].

Described specifically, the target taxane derivative (1) is available by providing 10-deacetylbaccatin III (2), a known compound, as a raw material, (3) protecting its 7-hydroxyl group with a trialkylsilyl group, (4) introducing a water-solubility-imparting A group into the 10-hydroxyl group, (5) oxazolidinecarboxylating the 13-hydroxyl group, (6) deprotecting the 7-hydroxyl group and carrying out ring opening, and then introducing a group —COX into the amino group.

The protection of the 7-hydroxyl group of 10-deacetylbaccatin III can be carried out in a known manner, more specifically, by treating with a trialkylsilyl chloride in pyridine. As the protecting group, a trialkylsilyl group is preferred, with a tri($C_{1-6}$ alkyl)silyl group being more preferred and a triethylsilyl group being particularly preferred.

The 10-hydroxyl group of compound (3) is then acylated and the side chain (A-) having a function to impart water solubility is introduced.

Examples of the acylating method can include a method making use of the above-exemplified acid derivative in the presence of a suitable base and a method making use of a coupling agent.

Illustrative of the acylating reagent usable for the above acylation are acid chlorides, acid anhydrides and acid esters, and derivatives equivalent to these acylating reagents.

As a specific method for introducing the group (A-), 4-dimethylaminopiperidinocarbonylation, for example, can be achieved by conducting treatment with 4-dimethylaminopiperidinocarbonyl chloride in the presence of a suitable base (for example, n-butyl lithium) while using a solvent such as THF.

The 13-hydroxyl group is then oxazolidinecarboxylated to obtain the compound (5). The oxazolidinecarboxylation may be conducted, for example, by reacting a derivative of oxazolidinecarboxylic acid, e.g., N-benzyloxycarbonyl (Cbz)-2,2-dimethyl-4-phenyl-oxazolidinecarboxylic acid, DCC, dimethylaminopyridine (DMAP) or the like with the compound (4).

Next, the ring opening of the oxazolidine ring can be achieved by treating the resulting compound (5) with an acid in a solvent such as ethanol, thereby deprotecting (removing TES), and then conducting catalytic reduction in the presence of palladium-carbon, whereby the compound (6) can be obtained.

The compound (6) can be converted into the invention compound (1) by acylation of its amino group. The acylation can be carried out using the corresponding acid halide, acid anhydride or the like in the presence of a coupling agent such as a base.

The taxane derivative (1) according to the present invention was confirmed to have excellent antitumor activities in a test (Test 2) which was conducted by using, as an index, growth inhibition effects against KB cells.

As the taxane derivative (1) and the salt thereof according to the present invention have very high solubility in water (1,000-fold or higher compared with Taxol), they can be used for drugs such as injections without using any special solvent. As drug preparations, injections such as intravenous injections or intramuscular injections are preferred. In addition to such injections, they can also be formulated into liquid preparations such as inhalations, syrups or emulsions; solid preparations such as tablets, capsules or granules; or external preparations such as ointments or suppositories.

These preparations may generally contain ordinarily employed additives such as dissolution aids, stabilizers, humectants, emulsifiers, absorption enhancers and surfactants, as needed. Illustrative of these carriers are injection-grade distilled water, Ringer's injection, glucose, sucrose syrup, gelatin, edible oil, cacao butter, magnesium stearate, and talc.

The amount of the taxane derivative (1) contained in each of the above-described respective drug preparation varies depending on the conditions of a patient to whom the drug preparation is administered, its preparation form and the like. In general, however, its amount per unit dosage form may desirably range from about 0.5 to 100 mg in the case of injections, from about 5 to 1,000 mg in the case of oral preparations, and from about 5 to 1,000 mg in the case of suppositories. Further, the daily dosage of the drug having the above-described dosage forms varies depending on the condition, body weight, age, sex and the like of each patient and cannot be determined in a wholesale manner. Nonetheless, the daily dosage may generally be about 0.1 to 50 mg/kg, preferably about 1 to 20 mg/kg per adult. It is preferred to administer this dosage as a single dose or in divided dosage forms, two to four times a day.

The present invention will next be described in further detail by Examples. It should however be borne in mind that the present invention is not limited to them.

EXAMPLE 1

13-O-(3-Benzyloxycarbonyl-2,2-dimethyl-4-phenyl-5-oxazolidinecarbonyl)-10-O-(4-methylpiperazinocarbonyl)-7-O-triethylsilyl-10-deacetylbaccatin III (Compound a)

In toluene was dissolved 10-O-(4-methylpiperazinocarbonyl)-7-O-triethylsilyl-10-deacetylbaccatin III (240 mg, 0.31 mmol), followed by the addition of 3-benzyloxycarbonyl-2,2-dimethyl-4-phenyl-5-oxazolidinecarboxylic acid (325 mg, 0.91 mmol), DCC (206 mg, 1.0 mmol) and DMAP (12 mg). The resulting mixture was stirred at room temperature for 3 hours. The reaction mixture was filtered. After the filtrate was concentrated, the residue was washed with a saturated aqueous solution of sodium bicarbonate and extracted with chloroform. The organic layer was dried over anhydrous magnesium sulfate, the solvent was distilled off under reduced pressure, and the residue was purified by chromatography on a silica gel column (chloroform-methanol mixed solvent [93:7]), whereby the title compound (309 mg, 89%) was obtained.

$^1$H-NMR (CDCl$_3$) δ: 0.56(m,6H), 0.90(t,J=8 Hz,9H), 1.17(s,3H), 1.18(s,3H), 1.63(s,3H), 1.74(s,3H), 1.80(s,3H), 1.88(m,1H,C$_6$—H), 1.90(s,3H)), 2.08(s,3H), 2.14(d,J=10 Hz,2H), 2.25–2.72(m,5H), 2.37(s,3H), 3.35–3.75(m,4H), 3.78(d,J=7 Hz,1H,C$_3$—H), 4.09(d,J=8 Hz,1H,C$_{20}$—H), 4.23 (d,J=8HZ,1H,C$_{20}$—H), 4.43(dd,J=10,7 Hz,1H,C$_7$—H), 4.49 (d,J=5 Hz,1H), 4.82–5.16(m,2H), 4.86(d,J=8 Hz,1H,C$_5$—H), 5.21(s,1H), 5.63(d,J=7 Hz,1H,C$_2$—H), 6.21(t,J=8 Hz,1H,C$_{13}$—H), 6.36(s,1H,C$_{10}$—H), 6.74(br,1H), 7.08–7.33(m,9H), 7.46(t,J=8 Hz,2H), 7.60(t,J=7 Hz,1H), 8.02(d,J=7 Hz,2H).

EXAMPLE 2

13-O-[3-(2-Furoylamino)-2-hydroxy-3-phenylpropionyl]-10-O-(4-methylpiperazinocarbonyl)-10-deacetylbaccatin III (Compound b)

The compound a (43 mg, 0.04 ml) of Example 1 was dissolved in ethanol (4 ml), followed by the addition of 0.1N-hydrochloric acid (4 ml). The resulting mixture was stirred at room temperature for 17 hours. The solvent was distilled off under reduced pressure. A saturated aqueous solution of sodium bicarbonate was added to the residue for washing, followed by extraction with chloroform. The organic layer was dried over anhydrous magnesium sulfate and then distilled under reduced pressure to remove the solvent. To the residue were added methanol (5 ml), water (0.5 ml) and 10% palladium carbon (20 mg) and the resulting mixture was stirred for 4 hours at normal temperature and normal pressure under a hydrogen gas atmosphere. After the reaction mixture was filtered through a Celite pad and the filtrate was concentrated, methylene chloride (10 ml) was added to the residue to dissolve the latter in the former. To the resulting solution were added 2-furoyl chloride (4 mg, 0.03 mmol) and triethylamine (0.03 mmol), followed by stirring for 2 hours over an ice bath. The reaction mixture was then washed with a saturated aqueous solution of sodium bicarbonate and extracted with chloroform. The organic layer was dried over anhydrous magnesium sulfate, the solvent was distilled off under reduced pressure and the residue was purified by chromatography on a silica gel column (chloroform-methanol mixed solvent [19:1]). Further purification was conducted by reverse-phase high-performance liquid chromatography (eluent: 10 mM potassium dihydrogenphosphate-acetonitrile [1:2]), whereby the title compound (25 mg, 72%) was obtained.

$^1$H-NMR (CDCl$_3$) δ: 1.11(s,3H), 1.22(s,3H), 1.66(s,3H), 1.81(s,3H), 1.85(m,1H,C$_6$—H), 2.24–2.29(m,2H,C$_{14}$—H), 2.35(s,6H), 2.43–2.65(m,5H), 3.09(s,1H), 3.37–3.75(m,4H), 3.77(d,J=7 Hz,1H,C$_3$·—H), 4.18(d,J=8 Hz,1H,C$_{20}$H), 4.27 (d,J=8 Hz,1H,C$_{20}$—H), 4.41(m,1H,C$_7$—H), 4.75(d,J=2 Hz,1H,C$_2$·—H), 4.93(d,J=8 Hz,1H,C$_5$—H), 5.64(d,J=7 Hz,1H,C$_2$—H), 5.72(dd,J=9.2 Hz,1H,C$_3$·—H), 6.22(t,J=8 Hz,1H,C$_{13}$—H), 6.23(s,1H,C$_{10}$—H), 6.45(dd,J=3.2 Hz,1H), 7.00(d,J=4 Hz,1H), 7.14(d,J=9 Hz,1H,NH), 7.31–7.48(m, 6H), 7.52(t,J=8 Hz,2H), 7.61(t,J=8 Hz,1H), 8.11(d,J=7 Hz,2H); SI-MS m/z: 929[M+H]+.

EXAMPLE 3

13-O-[3-(2-Thenoylamino)-2-hydroxy-3-phenylpropionyl]-10-O-( 4-methylpiperazinocarbonyl)-10-deacetylbaccatin III (Compound c)

Using the compound a (37 mg, 0.03 mmol) of Example 1 and 2-thenoyl chloride (4 mg, 0.03 mmol), reaction and after-treatment were conducted as in Example 2, whereby the title compound (8 mg, 26%) was obtained.

$^1$H-NMR (CDCl$_3$) δ: 1.05(s,3H), 1.16(s,3H), 1.61(s,3H), 1.76(s,3H), 1.81(m,1H,C$_6$—H), 2.07–2.27(m,2H,C$_{14}$—H), 2.31(s,3H), 2.39(s,3H), 2.38–2.75(m,5H), 2.97(s,1H), 3.38–3.80(m,4H), 3.71(d,J=7 Hz,1H,C$_3$·—H), 4.13(d,J=8 Hz,1H,C$_{20}$—H), 4.22(d,J=8 Hz,1H,C$_{20}$—H), 4.35(m,1H, C$_7$—H), 4.72(d,J=2 Hz,1H,C$_2$·—H), 4.88(d,J=10 Hz,1H, C$_5$—H), 5.59(d,J=7 Hz,1H,C$_2$—H), 5.70(dd,J=9.2 Hz,1H, C$_3$·—H), 6.15(t,J=8 Hz,1H,C$_{13}$—H), 6.18(s,1H,C$_{10}$—H), 6.84(d,J=8 Hz,1H,NH), 7.00(m,1H), 7.28–7.41(m,7H), 7.64 (t,J=7 Hz,2H), 7.55(t,J=7 Hz,1H), 8.06(d,J=8 Hz,2H); SI-MS m/z: 944[M+H]+.

EXAMPLE 4

13-O-[3-Isonicotinoylamino-2-hydroxy-3-phenylpropionyl]-10-O-(4-methylpiperazinocarbonyl)-10-deacetylbaccatin III (Compound d)

Using the compound a (37 mg, 0.03 mmol) of Example 1 and isonicotinoyl chloride hydrochloride (5 mg, 0.03 mmol), reaction and after-treatment were conducted as in Example 2, whereby the title compound (1.3 mg, 4%) was obtained.

$^1$H-NMR (CDCl$_3$) δ: 1.08(s,3H), 1.22(s,3H), 1.65(s,3H), 1.79(s,3H), 1.86(m,1H,C$_6$—H), 2.20–2.33(m,2H,C$_{14}$—H), 2.37(s,3H), 2.50(s,3H), 2.42–2.95(m,5H), 3.10(s,1H), 3.40–3.85(m,4H), 3.76(d,J=7 Hz,1H,C$_3$·—H), 4.17(d,J=9 Hz,1H,C$_{20}$—H), 4.29(d,J=8 Hz,1H,C$_{20}$—H), 4.40(m,1H, C$_7$—H), 4.78(d,J=3 Hz,1H,C$_2$·—H), 4.93(d,J=9 Hz,1H, C$_5$—H), 5.63(d,J=7 Hz,1H,C$_2$—H), 5.77(dd,J=9.2 Hz,1H, C$_3$·—H), 6.22(t,J=9 Hz,1H,C$_{13}$—H), 6.24(s,1H,C$_{10}$—H), 7.22–7.61(m,11H), 8.11(d,J=7 Hz,2H), 8.68(m,1H).

EXAMPLE 5

13-O-(3-Hexanoylamino-2-hydroxy-3-phenylpropionyl)-10-O-(4-methylpiperazinocarbonyl)-10-deacetylbaccatin III (Compound e)

Using the compound a (37 mg, 0.03 mmol) of Example 1 and hexanoyl chloride (2.7 mg, 0.02 mmol), reaction and after-treatment were conducted as in Example 2, whereby the title compound (11 mg, 35%) was obtained.

$^1$H-NMR (CDCl$_3$) δ: 0.81(t,J=7 Hz,3H), 1.12(s,3H), 1.19–1.27(m,4H), 1.50–1.59(m,2H), 1.66(s,3H), 1.82(s,3H), 1.85(m,1H,C$_6$—H), 2.17(t,J=7 Hz,2H), 2.21–2.31(m,2H, C$_{14}$—H), 2.32(s,3H), 2.33(s,3H), 2.41–2.57(m,5H), 3.09(s, 1H), 3.33–3.75(m,4H), 3.76(d,J=7 Hz,1H,C$_3$·—H), 4.17(d, J=8 Hz,1H,C$_{20}$—H), 4.27(d,J=8 Hz,1H,C$_{20}$—H), 4.41(m, 1H,C$_7$—H), 4.66(d,J=3 Hz,1H,C$_2$·—H), 4.93(d,J=8 Hz,1H, C$_5$—H), 5.56(dd,J=9.3 Hz,1H,C$_3$·—H), 5.64(d,J=7 Hz,1H, C$_2$—H), 6.17(d,J=9 Hz,1H,NH), 6.18(t,J=9 Hz,1H,C$_{13}$—H), 6.24(s,1H,C$_{10}$—H), 7.30–7.39(m,5H), 7.49(t,J=8 Hz,2H), 7.59(t,J=7 Hz,1H), 8.09(d,J=7 Hz,2H); SI-MS m/z: 931[M+H]+.

EXAMPLE 6

13-O-(3-Isopropyloxycarbonylamino-2-hydroxy-3-phenylpropionyl)-10-O-(4-methylpiperazinocarbonyl)-10-deacetylbaccatin III (Compound f)

Using the compound a (71 mg, 0.06 mmol) of Example 1 and isopropyl chloroformate (7.4 mg, 0.06 mmol), reaction and after-treatment were conducted as in Example 2, whereby the title compound (29 mg, 50%) was obtained.

$^1$H-NMR (CDCl$_3$) δ: 1.07(s,3H), 1.13(d,J=6 Hz,6H), 1.24 (s,3H), 1.65(s,3H), 1.84(s,3H), 1.86(m,1H,C$_6$—H), 2.18–2.26(m,2H,C$_{14}$—H), 2.35(s,3H), 2.38–2.65(m,5H), 2.39(s,3H), 3.09(s,1H), 3.40–3.75(m,4H), 3.77(d,J=7 Hz,1H,C$_3$·—H), 4.15(d,J=8 Hz,1H,C$_{20}$—H), 4.28(d,J=8 Hz,1H,C$_{20}$—H), 4.39(m,1H,C$_7$—H), 4.62(d,J=2 Hz,1H, C$_2$·—H), 4.75(m,1H), 4.93(d,J=8 Hz,1H,C$_5$—H), 5.28(br, 1H,NH), 5.45(dd,J=9.2 Hz,1H,C$_3$·—H), 5.63(d,J=7 Hz,1H, C$_2$—H), 6.24(s,1H,C$_{10}$—H), 6.25(t,J=8 Hz,1H,C$_{13}$—H), 7.29–7.40(m,5H), 7.48(t,J=8 Hz,2H), 7.59(t,J=7 Hz,1H), 8.09(d,J=7 Hz,2H); SI-MS m/z: 921[M+H]+.

EXAMPLE 7

13-O-(3-Benzyloxycarbonyl-2,2-dimethyl-4-phenyl-5-oxazolidinecarbonyl)-10-O-(4-ethylpiperazinocarbonyl)-7-O-triethylsilyl-10-deacetylbaccatin III (Compound g)

Using 10-O-(4-ethylpiperazinocarbonyl)-7-O-triethylsilyl-10-deacetylbaccatin III (200 mg, 0.25 mmol), reaction and after-treatment were conducted as in Example 1, whereby the title compound (268 mg, 93%) was obtained.

$^1$H-NMR (CDCl$_3$) δ: 0.56(m,6H), 0.90(t,J=8 Hz,9H), 1.06–1.20(m,9H), 1.68(s,3H), 1.74(s,3H), 1.80(s,3H), 1.87 (m,1H,C$_6$—H), 1.90(s,3H), 2.08(s,3H), 2.14(d,J=9 Hz,2H), 2.26–2.80(m,7H), 3.40–3.98(m,4H), 3.78(d,J=7 Hz,1H, C$_3$·—H), 4.08(d,J=9 Hz,1H,C$_{20}$—H), 4.23(d,J=8 Hz,1H, C$_{20}$—H), 4.43(dd,J=11.7 Hz,1H,C$_7$—H), 4.49(d,J=6 Hz,1H), 4.85–5.12(m,2H), 4.86(d,J=8 Hz,1H,C$_5$—H), 5.22 (s,1H), 5.63(d, J=7 Hz,1H,C$_2$—H), 6.21(t,J=9 Hz,1H,C$_{13}$—H), 6.36(s,1H,C$_{10}$—H), 6.74(br,1H), 7.04–7.33(m,9H), 7.46 (t,J=8 Hz,2H), 7.60(t,J=8 Hz,1H), 8.02(d,J=8 Hz,2H).

EXAMPLE 8

13-O-(3-Neopentyloxycarbonylamino-2-hydroxy-3-phenylpropionyl)-10-O-(4-ethylpiperazinocarbonyl)-10-deacetylbaccatin III (Compound h)

Using the compound g (70 mg, 0.06 mmol) of Example 7 and neopentyl-p-nitrophenylcarbonate (15 mg, 0.06 mmol), reaction and after-treatment were conducted as in Example 2, whereby the title compound (24 mg, 41%) was obtained.

$^1$H-NMR (CDCl$_3$) δ: 0.79(s,9H), 1.11(s,3H), 1.13(s,3H), 1.24(s,3H), 1.65(s,3H), 1.84(s,3H), 1.86(m,1H,C$_6$—H), 2.14–2.30(m,2H,$C_{14}$—H), 2.39(s,3H), 2.40–2.65(m,7H), 3.11(s,1H), 3.38–3.76(m,4H), 3.59(d,J=10 Hz,2H), 3.77(d, J=7 Hz,1H,$C_3$—H), 4.15(d,J=9 Hz,1H,$C_{20}$—H), 4.27(d,J=9 Hz,1H,$C_{20}$—H), 4.42(m,1H,$C_7$—H), 4.64(s,1H,$C_2$,—H), 4.93(d,J=8 Hz,1H,$C_5$—H), 5.31(br,1H,NH), 5.54(d,J=9 Hz,1H,$C_3$—H), 5.63(d,J=7 Hz,1H,$C_2$—H), 6.23(s,1H, $C_{10}$—H), 6.24(t,J=9 Hz,1H,$C_{13}$—H), 7.31–7.39(m,5H), 7.48(t,J=8 Hz,2H), 7.59(t,J=7 Hz,1H), 8.10(d,J=7 Hz,2H); SI-MS m/z: 962[M+H]+.

EXAMPLE 9

13-O-[3-(tert-Amyloxycarbonylamino)-2-hydroxy-3-phenylpropionyl]-10-O-(4-ethylpiperazinocarbonyl)-10-deacetylbaccatin III (Compound i)

Using the compound g (54 mg, 0.05 mmol) of Example 7 and di-tert-amyl dicarbonate (15 mg, 0.06 mmol), reaction and after-treatment were conducted as in Example 2, whereby the title compound (23 mg, 51%) was obtained.

$^1$H-NMR (CDCl$_3$) δ: 0.76(t,J=7 Hz,3H), 1.11(s,3H), 1.24 (s,3H), 1.27(s,6H), 1.64–1.68(m,5H), 1.85(s,3H), 1.86(m, 1H,$C_6$—H), 2.04–2.30(m,2H,$C_{14}$—H), 2.36(s,3H), 2.42–2.61(m,7H), 3.27(s,1H), 3.35–3.75(m,4H), 3.77(d,J=7 Hz,1H,$C_3$—H), 4.15(d,J=8 Hz,1H,$C_{20}$—H), 4.28(d,J=8 Hz,1H,$C_{20}$—H), 4.42(m,1H,$C_7$—H), 4.61(s,1H,$C_2$,—H), 4.94(d,J=9 Hz,1H,$C_5$—H), 5.26(br,1H,NH), 5.34(d,J=10 Hz,1H,$C_3$,—H), 5.64(d,J=7 Hz,1H,$C_2$—H), 6.23(m,1H, $C_{13}$—H), 6.25(s,1H,$C_{10}$—H), 7.31–7.41(m,5H), 7.48(t,J=8 Hz,2H), 7.60(t,J=7 Hz,1H), 8.09(d,J=8 Hz,2H); SI-MS m/z: 962[M+H]+.

EXAMPLE 10

13-O-(3-Cyclopentyloxycarbonylamino-2-hydroxy-3-phenylpropionyl)-10-O-(4-ethylpiperazinocarbonyl)-10-deacetylbaccatin III (Compound j)

Using the compound g (54 mg, 0.05 mmol) of Example 7 and cyclopentyl chloroformate (7 mg, 0.05 mmol), reaction and after-treatment were conducted as in Example 2, whereby the title compound (25 mg, 55%) was obtained.

$^1$H-NMR (CDCl$_3$) δ: 1.11(s,3H), 1.25(s,3H), 1.38–1.75 (m,8H), 1.65(s,3H), 1.83(s,3H), 1.85(m,1H,$C_6$—H), 2.22–2.30(m,2H,$C_{14}$—H), 2.35(s,3H), 2.40–2.65(m,7H), 3.30(s,1H), 3.35–3.73(m,4H), 3.77(d, J=7 Hz,1H,$C_3$—H), 4.16(d,J=9 Hz,1H,$C_{20}$—H), 4.28(d,J=9 Hz,1H,$C_{20}$—H), 4.42(m,1H,$C_7$—H), 4.62(s,1H,$C_2$,—H), 4.90(m,1H), 4.93(d, J=7 Hz,1H,$C_5$—H), 5.28(br,1H,NH), 5.41(d,J=9 Hz,1H, $C_3$,—H), 5.65(d,J=7 Hz,1H,$C_2$—H), 6.24(m,1H,$C_{13}$—H), 6.25(s,1H,$C_{10}$—H), 7.31–7.40(m,5H), 7.48(t,J=8 Hz,2H), 7.60(t,J=7 Hz,1H), 8.10(d,J=7 Hz,2H). SI-MS m/z: 960[M+H]+.

EXAMPLE 11

13-O-(3-Cyclohexyloxycarbonylamino-2-hydroxy-3-phenylpropionyl)-10-O-(4-ethylpiperazinocarbonyl)-10-deacetylbaccatin III (Compound k)

Using the compound g (40 mg, 0.035 mmol) of Example 7 and cyclohexyl-p-nitrophenyl carbonate (13 mg, 0.05 mmol), reaction and after-treatment were conducted as in Example 2, whereby the title compound (3 mg, 9%) was obtained.

$^1$H-NMR (CDCl$_3$) δ: 1.02–1.75(m,10H), 1.06(s,3H), 1.20 (s,3H), 1.60(s,3H), 1.80(s,3H), 1.81(m,1H,$C_6$—H), 2.17–2.30(m,2H,$C_{14}$—H), 2.33(s,3H), 2.42–2.78(m,7H), 3.02(s,1H), 3.40–3.80(m,4H), 3.72(d,J=7 Hz,1H,$C_3$—H), 4.10(d,J=9HZ,1H,$C_{20}$—H), 4.22(d,J=9 Hz,1H,$C_{20}$—H), 4.36(m,1H), 4.39(m,1H,$C_7$—H), 4.59(s,1H,$C_2$,—H), 4.89(d, J=7 Hz,1H,$C_5$—H), 5.26(d,J=9 Hz,1H,NH), 5.40(d,J=9 Hz,1H,$C_3$,—H), 5.58(d,J=7 Hz,1H,$C_2$—H), 6.20(s,1H, $C_{10}$—H), 6.22(m,1H,$C_{13}$—H), 7.26–7.34(m,5H), 7.44(t,J=8 Hz,2H), 7.55(t,J=7 Hz,1H) 8.06(d,J=8 Hz,2H); SI-MS m/z: 974[M+H]+.

EXAMPLE 12

13-O-(3-Benzyloxycarbonyl-2,2-dimethyl-4-phenyl-5-oxazolidinecarbonyl)-10-O-(4-piperidinopiperidinocarbonyl)-7-O-triethylsilyl-10-deacetylbaccatin III (Compound l)

Using 10-O-(4-piperidinopiperidinocarbonyl)-7-O-triethylsilyl-10-deacetylbaccatin III (120 mg, 0.14 mmol), reaction and after-treatment were conducted as in Example 1, whereby the title compound (161 mg, 97%) was obtained.

$^1$H-NMR (CDCl$_3$) δ: 0.56(m,6H), 0.89(t,J=8 Hz,9H), 1.17(s,3H), 1.18(s,3H), 1.41–2.02(m,11H), 1.65(s,3H), 1.74 (s,3H), 1.80(s,3H), 1.89(s,3H), 2.06(s,3H), 2.14(d,J=9 Hz,2H), 2.40–3.07(m,7H), 2.48(m,1H,$C_6$—H), 3.77(d,J=7 Hz,1H,$C_3$—H), 4.08(d,J=9 Hz,1H,$C_{20}$—H), 4.23(d,J=9 Hz,1H,$C_{20}$—H), 4.30(br,1H), 4.43(dd,J=11.7 Hz,1H,$C_7$—H), 4.49(d,J=6 Hz,1H), 4.86(d,J=10 Hz,1H,$C_5$—H), 4.87–5.10(m,2H), 5.21(s,1H), 5.63(d,J=7 Hz,1H,$C_2$—H), 6.20(t,J=9 Hz,1H,$C_{13}$—H), 6.35(s,1H,$C_{10}$—H), 6.74(br, 1H), 7.02–7.33(m,9H), 7.46(t,J=8 Hz,2H), 7.60(t,J=8 Hz,1H), 8.02(d,J=7 Hz,2H).

EXAMPLE 13

13-O-[3-(2-Furoylamino)-2-hydroxy-3-phenylpropionyl]-10-O-(4-piperidinopiperidinocarbonyl)-10-deacetylbaccatin III (Compound m)

Using the compound l (99 mg, 0.08 mmol) of Example 12 and 2-furoyl chloride (7.8 mg, 0.06 mmol), reaction and after-treatment were conducted as in Example 2, whereby the title compound (16 mg, 19%) was obtained.

$^1$H-NMR (CDCl$_3$) δ: 1.06(s,3H), 1.17(s,3H), 1.30–1.95 (m,11H), 1.60(s,3H), 1.75(s,3H), 2.19–2.27(m,2H,$C_{14}$—H), 2.30(s,3H), 2.38–3.10(m,8H), 3.51(s,1H), 3.72(d,J=7 Hz,1H,$C_3$—H), 4.12(d,J=9 Hz,1H,$C_{20}$—H), 4.23(d,J=9 Hz,1H,$C_{20}$—H), 4.09–4.25(m,2H), 4.36(m,1H,$C_7$—H), 4.70(m,1H,$C_2$,—H), 4.89(d,J=8 Hz,1H,$C_5$—H), 5.59(d,J=7 Hz,1H,$C_2$—H), 5.68(dd,J=11.3 Hz,1H,$C_3$—H), 6.15(m,1H, $C_{13}$—H), 6.16(s,1H,$C_{10}$—H), 6.40(dd,J=4.2 Hz,1H), 7.95 (d,J=3 Hz,1H), 7.09(d,J=9 Hz,1H,NH), 7.26–7.42(m,6H), 7.45(t,J=8 Hz,2H), 7.56(t,J=7 Hz,1H), 8.07(d,J=8 Hz,2H); SI-MS m/z: 996[M+H]+.

EXAMPLE 14

13-O-[3-(3-Furoylamino)-2-hydroxy-3-phenylpropionyl]-10-O-(4-piperidinopiperidinocarbonyl)-10-deacetylbaccatin III (Compound n)

Using the compound l (60 mg, 0.05 mmol) of Example 12, 3-furoic acid (7.8 mg, 0.06 mmol) and DCC (0.06 mmol), reaction and after-treatment were conducted as in Example 2, whereby the title compound (13 mg, 26%) was obtained.

$^1$H-NMR (CDCl$_3$) δ: 1.11(s,3H), 1.21(s,3H), 1.40–1.98 (m,11H), 1.64(s,3H), 1.79(s,3H), 2.23(m,1H,$C_{14}$—H), 2.29

(m,1H,$C_{14}$—H), 2.34(s,3H), 2.40–3.10(m,8H), 3.16(s,1H), 3.76(d,J=7 Hz,1H,$C_3$—H), 4.09–4.27(m,2H), 4.16(d,J=8 Hz,1H,$C_{20}$—H), 4.26(d,J=9 Hz,1H,$C_{20}$—H), 4.40(m,1H, $C_7$—H), 4.74(m,1H,$C_{2'}$—H), 4.92(d,J=9 Hz,1H,$C_5$—H), 5.63(d,J=7 Hz,1H,$C_2$—H), 5.72(d,J=9 Hz,1H,$C_{3'}$—H), 6.21 (s,1H,$C_{10}$—H), 6.23(m,1H,$C_{13}$—H), 6.58(s,1H), 6.77(d,J=9 Hz,1H,NH), 7.29–7.44(m,6H), 7.49(t,J=8 Hz,2H), 7.60(t, J=7 Hz,1H), 7.88(m,1H), 8.10(d,J=8 Hz,2H); SI-MS m/z: 996[M+H]+.

EXAMPLE 15

13-O-(3-Benzyloxycarbonyl-2,2-dimethyl-4-phenyl-5-oxazolidinecarbonyl)-10-O-(4-dipropylaminopiperidinocarbonyl)-7-O-triethylsilyl-10-deacetylbaccatin III (Compound o)

Using 10-O-(4-dipropylaminopiperidinocarbonyl)-7-O-triethylsilyl-10-deacetylbaccatin III (710 mg, 0.82 mmol), reaction and after-treatment were conducted as in Example 1, whereby the title compound (760 mg, 77%) was obtained.

$^1$H-NMR (CDCl$_3$) δ: 0.56(m,6H), 0.90(t,J=7 Hz,9H), 0.92–1.02(m,6H), 1.16(s,3H), 1.17(s,3H), 1.24–1.96(m,9H), 1.63(s,3H), 1.74(s,3H), 1.80(s,3H), 1.89(s,3H), 2.00–3.14 (m,10H), 2.08(s,3H), 3.78(d,J=8 Hz,1H,$C_3$—H), 4.08(d,J=8 Hz,1H,$C_{20}$—H), 4.18–4.58(m,4H), 4.22(d,J=8 Hz,1H, $C_{20}$—H), 4.86(d,J=9 Hz,1H,$C_5$—H), 4.85–5.10(m,2H), 5.20 (s,1H), 5.62(d,J=7 Hz,1H,$C_2$—H), 6.21(m,1H,$C_{13}$—H), 6.36(s,1H,$C_{10}$—H), 6.68(br,1H), 7.05–7.50(m,9H), 7.46(t, J=8 Hz,2H), 7.60(t,J=7 Hz,1H), 8.02(d,J=8 Hz,2H).

EXAMPLE 16

13-O-(3-Neopentyloxycarbonylamino-2-hydroxy-3-phenylpropionyl)-10-O-(4-dipropylaminopiperidinocarbonyl)-10-deacetylbaccatin III (Compound p)

Using the compound o (76 mg, 0.06 mmol) of Example 15 and neopentyl-p-nitrophenyl carbonate (15 mg, 0.06 mmol), reaction and after-treatment were conducted as in Example 2, whereby the title compound (28 mg, 43%) was obtained.

$^1$H-NMR (CDCl$_3$) δ: 0.75(s,9H), 0.76–0.94(m,6H), 1.07 (s,3H), 1.19(s,3H), 1.30–1.98(m,6H), 1.60(s,3H), 1.82(s, 3H), 2.09–3.15(m,10H), 2.31(s,3H), 3.30(br,1H), 3.54(d,J= 10 Hz,1H), 3.64(d,J=10 Hz,1H), 3.72(d,J=7 Hz,1H,$C_3$—H), 4.05–4.23(m,2H), 4.11(d,J=8 Hz,1H,$C_{20}$—H), 4.22(d,J=8 Hz,1H,$C_{20}$—H), 4.37(m,1H,$C_7$—H), 4.60(s,1H,$C_{2'}$—H), 4.89(d,J=8 Hz,1H,$C_5$—H), 5.26(br,1H,NH), 5.48(br,1H, $C_{3'}$—H), 5.58(d,J=7 Hz,1H,$C_2$—H), 6.18(s,1H,$C_{10}$—H), 6.20(t,J=9 Hz,1H,$C_{13}$—H), 7.27–7.34(m,5H), 7.43(t,J=8 Hz,2H), 7.54(t,J=7 Hz,1H), 8.05(d,J=7 Hz,2H); SI-MS m/z: 1032[M+H]+.

EXAMPLE 17

13-O-[3-(tert-Amyloxycarbonylamino)-2-hydroxy-3-phenylpropionyl]-10-O-(4-dipropylaminopiperidinocarbonyl)-10-deacetylbaccatin III (Compound q)

Using the compound o (76 mg, 0.06 mmol) of Example 15 and di-tert-amyl dicarbonate (15 mg, 0.06 mmol), reaction and after-treatment were conducted as in Example 2, whereby the title compound (23 mg, 36%) was obtained.

$^1$H-NMR (CDCl$_3$) δ: 0.76(m,3H), 0.83–0.94(m,6H), 1.12 (s,3H), 1.25(s,3H), 1.27(s,6H), 1.36–1.96(m,11H), 1.65(s, 3H), 1.84(s,3H), 2.08–3.08(m,10H), 2.35(s,3H), 3.17(s,1H), 3.77(d,J=7 Hz,1H,$C_3$—H), 4.12–4.30(m,2H), 4.15(d,J=8 Hz,1H,$C_{20}$—H), 4.27(d,J=8 Hz,1H,$C_{20}$—H), 4.42(m,1H, $C_7$—H), 4.61(s,1H,$C_{2'}$—H), 4.94(d,8 Hz,1H,$C_5$—H), 5.26 (br,1H,NH), 5.36(d,J=10 Hz,1H,$C_{3'}$—H), 5.64(d,J=7 Hz,1H, $C_2$—H), 6.23(S,1H,$C_{10}$—H), 6.24(t,J=9 Hz,1H,$C_{13}$—H), 7.28–7.40(m,5H), 7.48(t,J=8 Hz,2H), 7.59(t,J=7 Hz,1H), 8.09(d,J=7 Hz,2H); SI-MS m/z: 1032[M+H]+.

TEST 1

Solubilities of Novel Water-soluble Taxane Derivatives

I) Measurement of the solubility of the compound (b)

1) Preparation of a calibration curve

The compound (b) was weighed in an amount of 1.19 mg, to which 1.19 ml of acetonitrile was added so that the compound was dissolved to provide a standard solution. Using a 10 μl portion of the standard solution, the test was conducted by HPLC (operation conditions 1). The peak area of the compound (b), which had been obtained from the chromatogram of the standard solution, was measured by automated integration. The peak area obtained as an average of three measurements was plotted against the amount (10.0 μg) of the compound (b) per 10 μl, whereby a calibration curve was prepared.

Calibration curve: Y=2.08×10$^{-5}$ X [X: peak area, Y: amount (μg) of the compound (b)]

[HPLC operation conditions 1]

Column: Inertsil ODS-2 (5–250), 40 deg.
Mobile phase: 0.01M KH$_2$PO$_4$—CH$_3$CN (3:2)
Flow rate: 1.0 ml/min.
Detection: Ultraviolet absorption photometer (225 nm), 0.2 aufs.

2) Solubility test of the compound (b)

The compound (b) was weighed in an amount of 4.0 mg and then suspended in 2.0 ml of purified water. To the resulting suspension, 45 μl (1.05 eq.) of 0.1N hydrochloric acid was added. By ultrasonication, the resulting mixture was formed into a uniform suspension, which was then shaken at room temperature for 2 hours. The thus-obtained mixture was filtered through a membrane filter (0.22 μm), and the filtrate was provided as a test solution. Using the resulting test solution, the test was conducted by HPLC (operation conditions 1). From the area obtained as an average of three measurements, the solubility of the compound (b) was determined.

Area (X) of the compound (b) obtained as an average of three measurements: 478747

Dissolved amount (Y) of the compound (b): 9.98 μg/5 μl (2.00 mg/ml)

II) Measurement of the solubility of the compound (j)

1) Preparation of a calibration curve

The compound (j) was weighed in an amount of 0.94 mg, to which 0.94 ml of acetonitrile was added so that the compound was dissolved to provide a standard solution. Using a 10 μl portion of the standard solution, the test was conducted by HPLC (operation conditions 1). The peak area of the compound (1), which had been obtained from the chromatogram of the standard solution, was measured by automated integration. The area obtained as an average of three measurements was plotted against the amount (10.0 μg) of the compound (j) per 10 μl, whereby a calibration curve was prepared.

Calibration curve: Y=2.02×10$^{-5}$ X [X: peak area, Y: amount (μg) of the compound (j)]

[HPLC operation conditions 1]

Column: Inertsil ODS-2 (5–250), 40 deg.
Mobile phase: 0.01M KH$_2$PO$_4$—CH$_3$CN (3:2)
Flow rate: 1.0 ml/min.

Detection: Ultraviolet absorption photometer (225 nm), 0.2 aufs.

2) Solubility test of the compound (j)

The compound (j) was weighed in an amount of 4.24 mg and then suspended in 2.0 ml of purified water. To the resulting suspension, 46 µl (1.05 eq.) of 0.1N hydrochloric acid was added. By ultrasonication, the resulting mixture was formed into a uniform suspension, which was then shaken at room temperature for 2 hours. The thus-obtained mixture was filtered through a membrane filter (0.22 µm), and the filtrate was provided as a test solution. Using the resulting test solution, the test was conducted by HPLC (operation conditions 1). From the area obtained as an average of three measurements, the solubility of the compound (j) was determined.

Area (X) of the compound (j) obtained as an average of three measurements: 456054

Dissolved amount (Y) of the compound (j): 9.20 µg/5 µl (1.84 mg/ml)

The above-described results and the solubility of Taxol are shown in Table 1 for comparison. It can be understood from Table 1 that the invention compounds have markedly high solubility in water.

TABLE 1

| Compound | Solubility (µg/ml) |
|---|---|
| Taxol | 0.4 |
| Compound b | 2000 |
| Compound j | 1840 |

TEST 2

Cancer Cell Proliferation Activities

Materials and procedures

Cells

As KB cells derived from a human mouth cancer, those purchased from Dainippon Pharmaceutical Co., Ltd. and stored in a lyophilized from at the Research Institute of that company was used. In Dulbecco's modified Eargle's medium containing 10% fetal bovine serum (product of NISSUI PHARMACEUTICAL CO., LTD.), the KB cells were cultured and maintained under the conditions of 5%, $CO_2$-air and 37° C.

Drugs

Each compound was used by dissolving it at a concentration of 10 mg/ml in DMSO.

Drug Treatment (1) KB

On Day-1, cells which were in a logarithmic growth phase were inoculated at 2,000 cells/100 µl/well on 96-well microtiter plates (Falcon #3072) by using a phenol-red-free culture medium with 10% fetal bovine serum contained therein (Dulbecco's modified Eargle's medium (Sigma)), and were cultured overnight. On Day 0, the compounds each of which had been diluted to 0.03 to 10,000 ng/ml with the same culture medium were added in 100 µl aliquots to the individual wells, and the cells were cultured for 3 days. Three wells were used per each drug concentration. Each plate was provided with three blank wells containing only the culture medium and also with eight wells as a drug-untreated control.

XTT Assay

Upon use, XTT (Sigma) was dissolved at a concentration of 1 mg/ml in each culture medium which was free of serum. Phenodin methosulfate (Sigma) dissolved at a concentration of 5 mM in PBS was added to the resulting solution at a volume ratio of 1/200. To each well, the solution so prepared was added in an amount of 50 µl per well. Subsequent to culture for 4 hours, OD was measured at 450 nm by ELISA.

Calculation of 50% Growth Inhibitory Concentration ($GI_{50}$)

$GI_{50}$ was calculated by interpolation from a concentration-growth inhibition rate (GIR). GIR was determined in accordance with the following formula:

$$GIR = 100 - \frac{OD_{Treated\,(Day\,3)} - OD_{Control\,(Day\,0)}}{OD_{Control\,(Day\,3)} - OD_{Control\,(Day\,0)}} \times 100$$

Test results are shown in Table 2.

TABLE 2

| | KB | |
|---|---|---|
| | $GI_{50}$ (ng/ml) | Activity ratio |
| Taxol | 1.3 | 1.0 |
| b | 1.4 | 0.9 |
| j | 0.58 | 2.2 |

Capability of Exploitation in Industry

The taxane derivatives according to the present invention have very high solubility in water, namely, water solubility as high as 1,000 times or more of Taxol, so that they can be formulated into liquid preparations such as injections without using any special solvent. In addition, they are also excellent in antitumor activities.

What is claimed is:

1. A taxane compound having the formula (1):

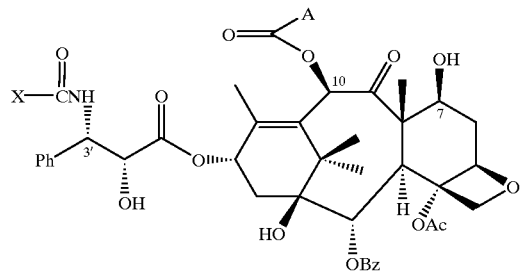

wherein:

A represents a group of the formula

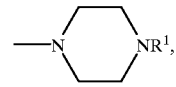

wherein $R^1$ is hydrogen, optionally substituted alkyl or benzyloxycarbonyl, or a group

wherein $R^2$ is amino, mono- or di-alkylamino or cyclic amino; X is alkyl, pyridyl, thienyl, furyl, cycloalkyloxy, isopropyloxy, neopentyloxy or tert-amyloxy; Y is hydrogen or trialkylsilyl; Ac is acetyl; Bz is benzoyl, and Ph is phenyl; or a pharmaceutically acceptable salt thereof.

2. The taxane compound of claim 1, wherein $R^1$ is alkyl having 1 to 6 carbon atoms, which is optionally substituted by monoalkylaminocarbonyl or dialkylaminocarbonyl.

3. The taxane compound of claim 1, wherein X is alkyl having 1 to 6 carbon atoms.

4. The taxane compound of claim 1, wherein X is $C_4$–$C_6$ cycloalkoxy.

5. The taxane compound of claim 1, wherein Y is hydrogen.

6. The taxane compound of claim 1, which is a hydrate.

7. The taxane compound of claim 1, which salt thereof is an anion salt selected from the group consisting of hydrochloride, hydroiodide, tartrate, acetate, maleate, methanesulfonate, succinate, and glutarate.

8. The taxane compound of claim 1, which salt thereof is an amino acid salt selected from the group consisting of arginine, lysine, and alanine.

9. A pharmaceutical composition comprising at least one of the taxane compounds or pharmaceutically acceptable salts thereof of claim 1, and a pharmaceutically acceptable carrier.

10. A method for treating a tumor, which comprises administering, to a patient suffering from the tumor, an effective amount of at least one taxane compound or pharmaceutically acceptable salt thereof as claimed in claim 1.

11. A process for preparing a taxane compound as defined in claim 1, which comprises:

a) protecting a 7-hydroxyl group of 10-diacetyl baccatin (III) with a trialkylsilyl group to form a compound of the formula (3):

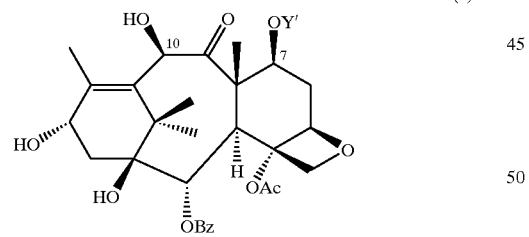

(3)

b) introducing a water-solubility-imparting A group into a 10-hydroxyl group to form a compound of the formula (4):

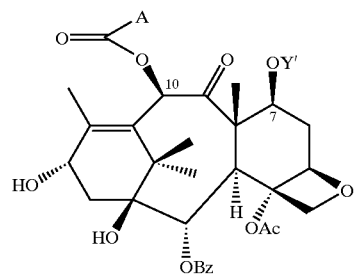

(4)

c) oxazolidine carboxylating a 13-hydroxyl group to form a compound of the formula (5):

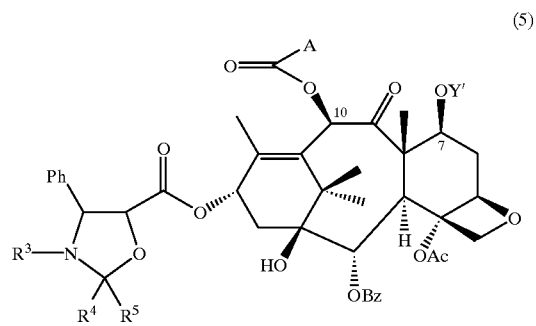

(5)

d) deprotecting the 7-hydroxyl group and effecting ring opening to form a compound of the formula (6):

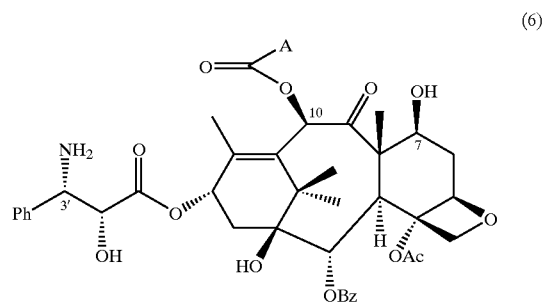

(6)

e) and then introducing a group COX into the amino group to form the taxane compound of the formula (1) or a pharmaceutically acceptable salt thereof, wherein A, Ac, Bz and Ph are as defined above; $R^3$ is hydrogen, alkoxycarbonyl or benzyloxycarbonyl; $R^4$ and $R^5$ each is hydrogen, alkyl, halogenoalkyl or alkxoyphenyl, with the proviso that $R^4$ and $R^5$ do not represent hydrogen at the same time or when either one of $R^4$ or $R^5$ represents halogenoalkyl or alkoxyphenyl, the other is hydrogen; and Y' is trialkylsilyl.

* * * * *